United States Patent [19]

Lee

[11] 3,941,834
[45] Mar. 2, 1976

[54] HIGH MOLECULAR WEIGHT ALIPHATIC HYDROCARBON SULFONIC ACIDS, SULFONYL CHLORIDES AND SULFONAMIDES

[75] Inventor: Richard J. Lee, Downers Grove, Ill.

[73] Assignee: Standard Oil Company, Chicago, Ill.

[22] Filed: June 9, 1971

[21] Appl. No.: 151,544

[52] U.S. Cl............ 260/504 R; 252/47.5; 252/48.2
[51] Int. Cl.$^2$........................................ C07B 13/00
[58] Field of Search.................... 260/513 R, 504 R

[56] References Cited
UNITED STATES PATENTS

| | | | |
|---|---|---|---|
| 2,166,981 | 7/1939 | Wiezevich et al. | 260/513 |
| 2,240,920 | 5/1941 | Werntz | 260/513 R |
| 2,365,783 | 12/1944 | Suter | 260/513 |
| 3,424,693 | 1/1969 | Stein et al. | 260/513 |
| 3,428,654 | 2/1969 | Rubinfeld et al. | 260/513 |
| 3,492,239 | 1/1970 | Baumann et al. | 260/513 |

*Primary Examiner*—James O. Thomas, Jr.
*Assistant Examiner*—A. Siegel
*Attorney, Agent, or Firm*—Fred R. Ahlers; Arthur G. Gilkes; William T. McClain

[57] ABSTRACT

Aliphatic hydrocarbon-substituted sulfonic acids, sulfonyl chlorides, amino sulfonic acids, sulfonamides and alkaline earth metal salts of such acids whose hydrocarbon substituent has an average molecular weight in the range of 300 to 200,000 are novel, useful compounds readily prepared through reaction of chlorosulfonic acid with a polymeric hydrocarbon having at least one carbon to carbon double bond as in the liquid to solid polypropene and polybutene or copolymer of two or more $C_2$ to $C_6$ unsaturated hydrocarbons having said average molecular weight. Such sulfonic acids, sulfonyl chlorides, amino sulfonic acids, sulfonamides and alkaline earth metal salts of the acid are soluble in hydrocarbon feeds (i.e., gasoline, diesel and heating fuels) and in lubricating oils as are the alkaline earth metal salts of such acids.

4 Claims, No Drawings

HIGH MOLECULAR WEIGHT ALIPHATIC HYDROCARBON SULFONIC ACIDS, SULFONYL CHLORIDES AND SULFONAMIDES

BACKGROUND OF THE INVENTION

Prior interest has centered on water-soluble alkyl sulfonates and sulfonamides having relatively short alkyl hydrocarbon (12–20 carbon) chains for their detergency properties in aqueous solutions. The starting sulfonic acids were prepared by the sulfonation of alkyl hydrocarbons or alcohols. For use with petroleum hydrocarbon fractions, mainly lubricating oil fractions, there has been some interest in oil-soluble guanidine salts of alkylsulfonic acids whose alkyl-substituent has a molecular weight in the range of about 200 to about 980, i.e. the alkyl substituent contains 14 to 70 carbon atoms. The use of such guanidine salts are described in U.S. Pat. No. 2,660,562. Briefly, that disclosure teaches that guanidine alkylsulfonates are oil-soluble gelling agents for grease preparation when the alkyl-substituent has from 14 to 24 carbon atoms, anti-rust agents when the alkyl-substituent contains 24 to 40 carbon atoms and detergency agents when the alkyl-substituent contains 40 to 70 carbon atoms.

However, at the time such guanidine alkylsulfonates were disclosed (1951) the severity requirements imposed by in-service use for crankcase lubricating oils was much less than the in-service use severity requirements of gasoline and diesel engines presently in use and under test for near future use with their anti-pollution devices. The guanidine alkylsulfonates which have alkyl radicals of 40 to 70 carbons (i.e. 560–980 MW) do not have a thermally stable structure and would not meet the present day higher in-service use severity requirements for crankcase lubricating oils.

Previously available alkaline earth metal alkylsulfonates have not, in general, been suitably acceptable anti-wear agents for crankcase lubricating oils and emphasis for that anti-wear function has been placed on oil-soluble calcium and magnesium alkylbenzene sulfonates and their over-based derivatives which also contributed anti-corrosion properties.

It has now been discovered that a sulfonic acid and sulfonyl chloride derived from liquid viscous to solid polymers of propene and butenes and copolymers of $C_2$ to $C_6$ unsaturated hydrocarbons having an average molecular weight in the range of 300 to 200,000 can be readily converted to the respective alkaline earth metal sulfonates or sulfonamides which are useful addition agents for hydrocarbon (gasoline, diesel and heating) fuels and lubricating oils because of their anti-deposition, detergency and viscosity improving (hydrocarbon portion has molecular weight above about 10,000) properties. Such metal sulfonates and sulfonamides are multi-functional. The sulfonic acid and sulfonyl chloride derivatives of such 300 to 200,000 average molecular weight hydrocarbon polymers are unique in and of themselves as are their preparation by the reaction of such hydrocarbon polymers with chlorosulfonic acid.

SUMMARY OF THE INVENTION

The present invention comprises the allylic sulfonic acid and sulfonyl chloride, vinyl sulfonic acid and sulfonyl chloride and $\beta$-chlorosulfonic acid and sulfonyl chloride of the polymeric hydrocarbons having one to two carbon to carbon double bond activated reaction sites which are polymers of propene, butenes and copolymers of $C_2$ to $C_6$ unsaturated hydrocarbons and which have an average molecular weight in the range of 300 to 200,000; their method of preparation and their alkaline earth metal salt, amino sulfonic acid and sulfonamide derivatives. Such sulfonic acids and their acid chlorides are obtained by directed reaction of chlorosulfonic acid with said polymeric hydrocarbon.

The reaction of chlorosulfonic acid (Cl SO$_3$H) with said polymeric hydrocarbons having 1 to 2 carbon to carbon activated reaction sites can result in three different conversions of the polymeric hydrocarbon according to the following three illustrative reactions:

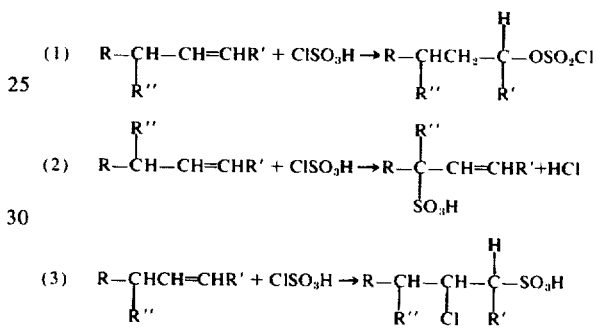

By further reaction of chlorosulfonic acid or through chloride or sulfuryl chloride the sulfonic acid of Reaction (2) there is obtained the corresponding sulfonyl chloride in the following manner:

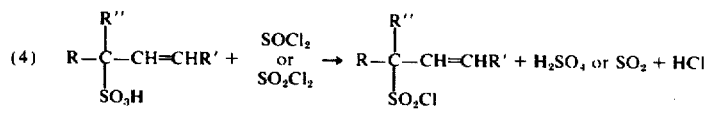

The beta-chloroalkyl sulfonic acid product of Reaction (3) can be thermally dehydrochlorinated to a vinyl sulfonic acid according to the following reaction:

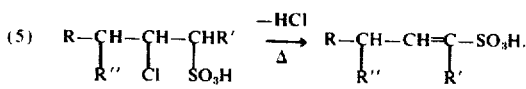

Said vinyl sulfonic acid can be reacted with sulfuryl chloride (SO$_2$Cl$_2$) or thionyl chloride (SO$_2$Cl$_2$) or chlorosulfonic acid to produce a vinyl sulfonyl chloride.

In the above illustrative reactions the polymeric hydrocarbon reactant shown has the substituent radicals R, R' and R'' whose total carbon and hydrogen content provide the average molecular weight range of 300 to 200,000 and which have the following defined significance. R is a hydrocarbon radical which can be straight- or branched-chain and consists of the main bulk of the molecule with 0 to 1 carbon to carbon double bond activated reactive site such as in the residue of the molecule:

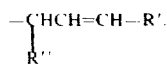

Such reactive cite, when present, can be a terminal site or a pendant site of the radical R.

R' can be hydrogen or a saturated alkyl hydrocarbon radical of 1 to 3 carbon atoms, for example methyl, ethyl, n-propyl and isopropyl.

R'' can be hydrogen or a saturated alkyl hydrocarbon radical of 2 to 5 carbon atoms.

All three different modes of conversion of the polymeric hydrocarbon with chlorosulfonic acid do not produce novel, useful oil-soluble products or intermediates. For example in Reaction (1) hydrogen of chlorosulfonic acid ($HO—SO_2Cl$) adds across the double bond and produces a polymeric hydrocarbon ester of chlorosulfuric acid. Such hydrocarbon esters of chlorosulfuric acid are thermally unstable and are readily subject to hydrolysis both at the chlorine and at the ester linkage to liberate sulfuric acid and HCl. Alkaline earth metal salts also hydrolyze to the acid sulfate and/or sulfate as do the amine derivatives. Hence, although the hydrocarbon ester of chlorosulfuric acid and its alkaline earth metal salt and amine derivatives are oil-soluble, their thermal instability and ready hydrolyzable nature producing undesirable by-products make them unsuitable for any known use especially as addition agents for fuels and lubricants.

However, the polymeric hydrocarbon- and chlorohydrocarbon-substituted sulfonic acids, their acid chlorides from or derivable from Reactions (2) and (3), e.g. by Reactions (4) and (5) are useful, thermally stable, hydrolysis resisting products as are their alkaline earth metal, amine, and sulfonamide derivative which are all soluble in petroleum fractions of the fuel and lubricating type fractions.

As previously illustrated, Reaction (2) produces allylic polymerhydrocarbon substituted allylic sulfonic acid from which its acid chloride can be obtained, and Reaction (3) produces a β-chloropolymeric hydrocarbon-substituted sulfonic acid which via Reaction (5) a polymeric hydrocarbon vinyl sulfonic acid is obtained which can be converted to its acid chloride. To achieve the results of Reactions (2) and (3) which differ in kind from the results of Reaction (1), aid must be provided to avoid formation of the polymer hydrocarbon ester of chlorosulfonic acid of Reaction (1). In general, low temperature conditions, e.g. downward from 100°F. provide such avoidance. The use of an ether-chlorosulfonic acid complex containing 0.5 to 1.0 mole chlorosulfonic acid per ether linkage with such use of low temperature are suitable for the additions of chlorosulfonic acid to polymeric hydrocarbon favoring β-chloro and α-sulfo introductions into the polymer molecule. Low temperature reaction favors polymer allylic sulfonic acid production.

The polymer hydrocarbon reactant of 300 to 200,000 average molecular weight varying from a viscous liquid to a semi-solid to solid and having 1 to 2 reactive sites activated by carbon-to-carbon double bonds are known compositions. The polypropenes and polybutenes and copolymers of propene and butene of the liquid viscous class have an average molecular weight in the 300 to 3,000 range and are obtained by polymerization of propene, isobutene; mixtures of isobutene with 1-butene and/or 2-butene; mixture consisting mainly of isobutene with minor amounts of 1- and 2-butene with still smaller amounts of butadiene as unsaturated compounds as in a $C_4$ hydrocarbon fraction; and mixtures of propene and such butene sources in the presence of Friedel-Crafts catalyst. Aluminum chloride is the catalyst of choice and the resulting hydrocarbon product, after removal of light ends in gasoline range is a mixture of 15–30% saturated hydrocarbons and 85–70% unsaturated hydrocarbons having more than one but less than two reactive carbon-to-carbon double bonds. Hydrogen transfer, common to such $AlCl_3$ catalysis, causes disproportionation and creates the saturated hydrocarbons. In such mixtures of 15–30% saturated polyalkyl hydrocarbon and 85–70% unsaturated hydrocarbons, the saturated and unsaturated hydrocarbon have substantially the same average molecular weights.

Polymers and copolymers from $C_2$–$C_6$ unsaturated hydrocarbons in the 500 to 3,500 average molecular weight range are known and they and their preparation are disclosed in U.S. Pat. No. 3,502,451. The method of preparation of such polymers and copolymers from $C_2$–$C_6$ unsaturated hydrocarbons is disclosed.

Additional polymeric hydrocarbons are those having limited numbers of double bonds include copolymers of ethylene with $C_3$ to $C_{18}$ linear or branched alphaolefins with an average ethylene content within the range of 60–80 mole percent degree of crystallinity of less than 25% and an average molecular weight in the range of 10,000 to 200,000. In said branched alphaolefin the branching occurs at least three carbon atoms removed from the double bond. The copolymers are prepared in the presence of catalysis provided by vanadium oxychloride and ethyl aluminum sesquichloride and have a characteristically low (less than 1.3%) decane insoluble (at 45°C.) polymer fraction. Those copolymers, their preparation and characterization are more fully described in U.S. Pat. No. 3,551,336.

Other polymeric hydrocarbons useful for the preparation of the sulfonic acid and sulfonyl chloride inventive intermediates are copolymers of (I) $C_2$–$C_{20}$ alpha-olefins and (II) $C_5$–$C_{20}$ diolefins in a mole ratio of (I) to (II) of 1.0–400:1.0 prepared in the presence of catalysis provided by a reducing metal compound and a reducible metal compound, i.e. Ziegler-Natta type catalysis for example a trialkyl aluminum compound and titanium tetrachloride at a temperature in the range of 30° to 150°C. at atmospheric pressure. Such copolymers can have a molecular weight in the range of 10,000 to 1,000,000 with the higher molecular weight products being obtained at the lower end of the temperature range. Typical illustration alphaolefins used are ethylene, propene, 1-butene, 1-pentane, 3-methyl-1-butene, 1-hexene, 1-heptene, 1-tetradecene and 1-octadecene. Typical diolefins are those having at least one terminal double bond illustrative of which are 1,5-hexadiene, 1,11-dodecadiene, 1,17-octadecadiene, 1,4-octadiene, 1,9-octadecadiene and 1,9,12-octadecadiene. Such copolymers have a structure:

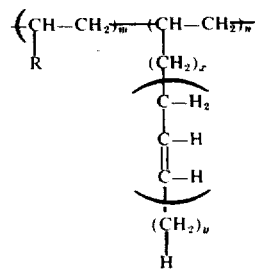

wherein R is hydrogen or $C_1$-$C_{18}$ aliphatic hydrocarbon radical, x is 0 to 15, y is 0–15, with the total of x and y being 0 to 18 and the mole ratio of m to n being 1.0–400:1.0. Such copolymers and their preparation are disclosed in U.S. Pat. No. 3,231,498.

Of the foregoing polymeric hydrocarbons those preferred as reactants with chlorosulfonic acid are the polymers of propene and isobutene and copolymers thereof with $C_2$-$C_6$ mono-olefinic hydrocarbons having a molecular weight in the range of 300 to 3000. Derivatives of the resulting sulfonic acids such as the sulfonamides and amino sulfonamides are excellent detergents for internal combustion engine fuels (gasoline and diesel fuel), heating fuels and lubricating oils. The polymeric hydrocarbons of the 10,000–200,000 molecular weight range when reacted with chlorosulfonic acid and converted to sulfonamides and amino sulfonamides provide multipurpose detergent-viscosity index improver addition agents.

For the preparation of sulfonamide and amine sulfonamide derivatives of the present inventive polymer hydrocarbon sulfonic acids there can be used any amine having at least one HN< group. Preferably the amine reactant is a primary amine of which the most preferred are diaminoalkanes, such as ethylene diamine, 1,3-diaminopropane, 1,2-diaminopropane, 1,8-diaminohexane, and the like containing 2 to 10 methylene groups; polyalkylene polyamine such as polyethylene and polypropylene polyamines having 2 to 10 alkylene groups and 3 to 11 amino groups; and polyethylene imines of 600 to 40,000 average molecular weight. Also useful are bis-(aminoalkyl) piperazine which are in nature diamino alkanes, whose aminoalkyl substituent: $H_2N$—R has 1 to 10 methylene groups as in aminomethyl; 1- and 2-aminoethyl; 1- and 2-aminomethylethyl; and the like aminobutyl, aminopentyl, aminohexyl, aminoheptyl, aminooctyl, aminononyl and aminodecyl substituent groups.

For the preparation of the sulfonamide and amino sulfonamide of this invention it is advantageous to conduct the reaction between the chlorosulfonic acid and the amine in the presence of a tertiary amine boiling at a temperature up to and including 240°F., preferably pyridine. The tertiary amine ties up the liberated HCl as a quaternary amine hydrochloride from which HCl can be readily removed by reaction with calcium oxide or hydroxide and filtration. The thus freed tertiary amine can be removed by heating with or without a gas purge (nitrogen is preferred as gas purge) at a temperature of from the boiling point up to 60°F. above the boiling point of the tertiary amine.

The preparation of sulfonamides of vinyl sulfonic acid involves straight forward two-step reactions. The vinyl sulfonic acid is converted into its acid chloride by its reaction with equal molar proportions of thionyl chloride or sulfuryl chloride as the first step. Then the resulting vinyl sulfonyl chloride is reacted with the amine having at least one HN< group; e.g. ammonia, alkylamine, diaminoalkane, polyalkylene polyamine or polyethylene polyimine, in the presence of tertiary amine (e.g. pyridine). The resulting product contains the vinyl sulfonamide moiety

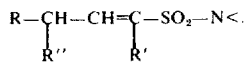

The preparation of sulfonamide derivatives of the β-chlorosulfonic acid obtained by Reaction 3 using the ether-chlorosulfonic acid complex reaction direction aid is readily accomplished by still further reactions. For example, reaction with thionyl chloride produces the corresponding β-chlorosulfonyl chloride as before indicated. This β-chlorosulfonyl chloride when reacted with one mole of an amine having the primary amine group $H_2N$- forms a cyclic sulfonamide believed to occur in the following manner:

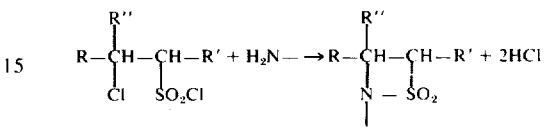

Reaction of the β-chlorosulfonic acid of Reaction 3 with an amine having at least one HN< group occurs first at the β-chlorine to form an internal amino salt (sulfobetaine):

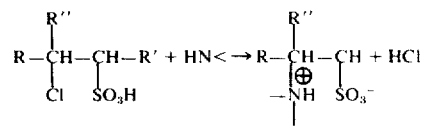

and such internal amino salt can be converted to an oil-soluble calcium carbonate salt of the sulfobetaine by reaction with calcium oxide or hydroxide and carbon dioxide in the presence of methanol:

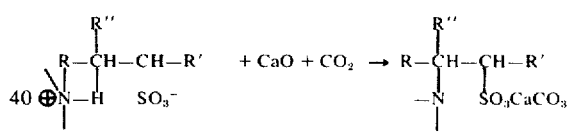

The allylic sulfonamides are readily prepared from the allylic sulfonyl chloride:

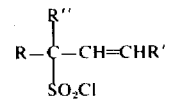

The preparation of the present inventive sulfonic acids, chlorosulfonic acids, beta-chlorosulfonic acids and their derivatives will be illustrated by the following examples as an aid to further understanding of compounds of this invention, their preparation and use.

EXAMPLE 1

Preparation of β-Chloro Polybutylsulfonic Acid

There are combined 1.0 liter of n-hexane and 1305 grams of polybutene of number average molecular weight ($\overline{Mn}$) 2219, (whose molecules 85% are unsaturated and 15% are saturated, to supply 0.5 mole unsaturated component). The hexane polybutene mixture is vigorously stirred and then an ether-chlorosulfonic acid complex of 0.5 mole (33 ml.) chlorosulfonic acid and 150 ml. of dimethoxyethane premixed at 30°F. is added at a rate controlled so that the temperature of the exothermic reaction did not exceed 90°F. The stirred reaction mixture is stirred for three hours at ambient temperature, 75°–77°F. The resulting solution contains 0.5 mole β-chloropolybutylsulfonic acid dissolved in a medium containing 196 grams saturated polybutyl hydrocarbon ($\overline{M}n$ 2219), 1.0 liter n-hexane and 130 grams dimethoxyethane.

EXAMPLE 2

Preparation of a β-amino Polybutylsulfobetaine

The reaction solution of Example 1 containing 0.3 mole of β-chloropolybutyl sulfonic acid is stirred at ambient temperature and 63 grams (0.3 mole) tetraethylene pentamine is added slowly to maintain a reaction temperature of 90°F. by the exothermic reaction. The amine substitution reaction is completed by stirring at ambient temperature overnight. For shorter completion of the amine substitution reaction, refluxing at n-hexane boiling point for two hours is adequate. Hydrogen chloride by-product of the amine substitution for the β-chlorine is removed by the addition of calcium hydroxide, the solution is heated to n-hexane reflux temperature and by-product water is distilled out and the resulting mixture is filtered over filter aid to remove solid calcium chloride. The filtrate is heated to 300°F. to remove solvents with the aid of nitrogen gas injection into the heated solution. The residue is the polybutyl sulfobetaine wherein the β-chlorine has been replaced with the tetraethylene pentamine moiety. The sulfobetaine is soluble in lubricating oil and readily forms a 40 weight percent solution in SAE-5W weight oil.

EXAMPLE 3

Preparation of Calcium Carbonate of Polybutyl Sulfobetaine

The sulfobetaine of Example 2 is dissolved in one liter of n-hexane and stirred at ambient temperature. The stirred solution there are added 0.6 mole (35 grams, a 100% excess) and 30 ml. of methanol. The stirred mixture is heated to the temperature of 140°F. and held at that temperature while carbon dioxide is injected into the solution through a dispersion tube for about 60 minutes. Solvent and by-product water are removed by heating to a temperature of 260°F. and injecting nitrogen gas into the heated liquid. The residue is calcium carbonate-sulfonate of polybutyl tetraethylene pentamine. This product is readily soluble in lubricant oil base stock, for example SAE-5W weight oil, at a concentration of 40 weight percent.

EXAMPLE 4

Preparation of Polybutyl Vinyl Sulfonylchloride

To a stirred solution containing 1305 grams of polybutene (0.5 mole unsaturated molecules) of $\overline{M}n$ 2219 dissolved in one liter of n-hexane there is added the ether complex of 0.5 mole chlorosulfonic acid in dimethoxyethane described in Example 1. The complex is added at a controlled rate so that the reaction temperature does not exceed 90°F. The stirred reaction mixture is then heated to the boiling point of n-hexane and nitrogen gas is injected into solution to assist in driving HCl from the solution as the hexane is refluxed. HCl evolution ceases in about 120 minutes under those conditions and in a shorter time at 260°–300°F. The HCl free hexane solution of polybutyl vinylsulfonic acid is cooled to ambient temperature and stirred while 0.5 mole (60 grams) thionyl chloride is added. This reaction mixture is heated until hexane reflux returns from a reflux condenser and such hexane reflux is maintained for 2 hours. Removal of sulfur dioxide and HCl by-product is assisted with injection of nitrogen gas into the hot stirred liquid. The residue left after distilling off n-hexane is 0.5 mole polybutyl vinylsulfonyl chloride whose polybutyl group has 2219 $\overline{M}n$.

EXAMPLE 5

Preparation of Polybutylvinyl Sulfonamide of Bis-Aminopropyl Piperazine

The polybutyl vinylsulfonyl chloride (0.5 mole) prepared as in Example 4 is dissolved in one liter of n-hexane. The solution is stirred at ambient temperature. To the stirred solution there is added 0.5 mole of bis-aminopropyl piperazine and 40 grams sodium hydroxide as catalyst dissolved in 120 ml. of water. The resulting mixture is heated to distill off a n-hexane-water azeotropic mixture. After by-product and added water are removed, the residual hexane solution is filtered to remove sodium chloride and the filtrate is heated to distill off with the aid of nitrogen gas injection the hexane solvent. The residue is polybutyl vinylsulfonamide of bis-aminopropyl piperazine which readily dissolves in lubricant oil base stock, e.g. SAE-5W weight oil, to form a solution of 40 weight percent of that sulfonamide.

EXAMPLE 6

Preparation of Polybutyl Vinylsulfonamide of Mono-polybutyl Imidazoline

The polybutyl vinylsulfonyl chloride (0.5 mole) prepared in Example 4 is dissolved in one liter of n-hexane. The solution is stirred at ambient temperature. To the stirred solution there is added 0.5 mole of mono-polybutyl imidazoline and 40 grams sodium hydroxide as catalyst dissolved in 120 ml. of water. The resulting mixture is heated to distill off a n-hexane-water azeotropic mixture. After by-product and added water are removed, the residual hexane solution is filtered to remove sodium chloride and the filtrate is heated to distill off with the aid of nitrogen gas injection the hexane solvent. The residue is polybutyl vinylsulfonamide of mono-polybutyl imidazoline which readily dissolves in lubricant oil base stock, e.g. SAE-5W weight oil, to form a solution of 40 weight percent of that sulfonamide.

EXAMPLE 7

Preparation of Polybutyl Allylic Sulfonylchloride

A solution of 2219 $\overline{M}n$ polybutene as described in Example 1 in 2.0 liters of n-hexane containing 0.7 mole of the unsaturated polybutene molecules is stirred and cooled to 60°F. To this solution there is added 0.7 mole chlorosulfonic acid dropwise and the exothermic reaction is not permitted to exceed 90°F. Stirring is continued about 60 minutes after all the chlorosulfonic acid has been added. Thereafter 1.1 mole of sulfuryl chloride is added with vigorous stirring of the solution. This reaction was maintained at a temperature not exceeding 80°F., and for the most part at 75°–77°F. After the addition of sulfuryl chloride, the reaction mixture is stirred one hour at ambient temperature and then heated until n-hexane refluxed. During n-hexane reflux nitrogen gas is injected into the solution to remove HCl split out. All HCl evolution ceased in about 3 hours. The resulting solution contains 0.7 mole of polybutyl allylic sulfonylchloride whose polybutyl group has 2219 $\overline{Mn}$. Said sulfonylchloride can be recovered by distilling off the remaining n-hexane solvent.

EXAMPLE 8

Preparation of Polybutyl Allylic Sulfonamide of Pentaethylene Hexamine

The 0.7 mole of polybutyl allylic sulfonylchloride prepared in Example 7 as a solution in 2 liters of n-hexane is stirred at ambient temperature and there is dropwise added thereto 72 grams (0.33 mole) of pentaethylene hexamine dissolved in 200 ml. of pyridine so that the exothermic reaction does not exceed 100°F. After all the amine solution is added, the stirred reaction mixture is heated to 300°F. with nitrogen gas injection to remove pyridine. Thereafter one mole of calcium hydroxide is added to neutralize HCl and the calcium chloride is removed by filtration over celite filter aid. The filtrate is heated to distill off remaining n-hexane solvent leaving as residue bis-polybutyl allylic sulfonamide of pentaethylene hexamine.

EXAMPLE 9

The method of Example 8 is repeated using an equal molecular amount (0.7 mole) of pentaethylene hexamine. The residue after distilling off remaining n-hexane solvent is mono-polybutyl allylic sulfonamide of pentaethylene pentamine.

Both of the products of Examples 8 and 9 are readily soluble in lubricant oil base stocks, e.g. SAE-5W weight oil, to form 40 weight percent solutions of those sulfonamides.

EXAMPLE 10

The sulfonamide of Example 9 is further reacted with a xylene solution containing 50 weight percent of $C_{23}$-polybutenyl substituted succinic anhydride. The sulfonamide and substituted succinic anhydride are used in equal molar proportions. This reaction is conducted with stirring and nitrogen gas injection under conditions which remove a water-xylene azeotropic mixture. After all the by-product water has been removed, the remaining xylene is distilled off. The residue is a polybutenylsuccinimide of the polybutyl allylic sulfonamide of pentaethylene hexamine which also is readily soluble in lubricant oil base stocks to form a 40 weight percent solution of the succinimide-sulfonamide reaction product.

EXAMPLE 11

A solution of 0.5 mole β-chloro-polybutyl (2219 $\overline{Mn}$) sulfonic acid in 1.0 liter of n-hexane and 195 grams polybutyl alkane of 2219 $\overline{Mn}$ is obtained by the reaction in 1.0 liter n-hexane of 2219 Mn polybutene containing 0.5 mole unsaturated species with ether complex of dimethoxyethane and chlorosulfonic acid to provide 0.5 mole thereof. The conditions for this preparation are those used in Example 1. After the one hour reaction completion with stirring at ambient temperature, 0.5 mole sulfuryl chloride is added to the stirred solution at a rate to keep the temperature of the reaction mixture just below 80°F., e.g. 76°–78°F. and the reaction is completed with stirring for one hour after sulfuryl chloride addition. Thereafter HCl and $SO_2$ are stripped from the stirred solution by injecting nitrogen gas into the liquid for 4 hours at ambient temperature. The resulting solution contains 0.5 mole β-chloro-polybutyl sulfonyl chloride.

To a part of the solution of the above prepared sulfonyl chloride containing 0.33 mole thereof there is added with stirring 0.33 mole of tetraethylene pentamine at a rate to obtain and maintain a reaction temperature of 90°F. of the stirred reaction mixture throughout the polyamine addition. Thereafter the reaction mixture is slowly heated to n-hexane reflux temperature, n-hexane reflux is continued for one hour, then 40 grams sodium hydroxide dissolved in 120 ml. of water are added, all the water is removed as a hexane-water azeotrope and then the remaining n-hexane is distilled off. The residue is a polybutyl alkane having two carbons of its carbon chain members of the azalkylene-substituted heterocyclic group as in the structure:

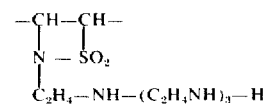

Such azalkylene-substituted cyclic sulfonamido-polybutyl alkanes are readily soluble in lubricant oil base stocks at least to the extent of forming a solution concentrate having up to 40 weight percent of such cyclic sulfonamido-containing compounds dissolved in lubricant oil base stocks as SAE-5W, SAE-10W, SAE-10, SAE-20, SAE-30 and SAE-40 weight oils.

EXAMPLE 12

A solution of 800 $\overline{Mn}$ polypropene in 1.0 liter of n-hexane to provide 0.5 mole of the unsaturated species of the polypropene is prepared. This solution is stirred, cooled to 60°F. and then 0.6 mole of chlorosulfonic acid is added slowly thereto so that the exothermic reaction does not exceed a temperature of 90°F. After addition of chlorosulfonic acid is completed the mixture is stirred for one hour at ambient temperature (e.g. 75°–77°F.). By-product HCl is removed by heating to n-hexane reflux temperature and nitrogen gas injection into the liquid. When HCl evolution from the reflux condenser ceases, the residual liquid is a solution of 0.5 mole of polypropyl-substituted allylic type sulfonic acid in n-hexane and saturated species of polypropene. The hydrocarbon portion of said sulfonic acid has a 800 $\overline{Mn}$. Removal of solvent by distillation leaves said sulfonic acid as residue.

EXAMPLE 13

The sulfonylchloride of the sulfonic acid of Example 12 is prepared in the following manner. The method of Example 12 is repeated through the one hour stirring at ambient temperature. Thereafter stirring is increased to vigorous and 1.0 mole of sulfuryl chloride is added to this stirred mixture and reaction temperature is maintained at 80°F. Then the reaction mixture is stirred one hour at ambient temperature after which the mixture is heated to n-hexane reflux temperature with nitrogen gas injection for 3 hours to remove by-product HCl and $SO_2$. The resulting liquid is a solution of 0.5 mole of polypropyl allylic type sulfonyl chloride whose hydrocarbon moiety has 800 $\overline{Mn}$ dissolved in n-hexane and saturated species of 800 $\overline{Mn}$ polypropene. Removal of solvent by distillation leaves said sulfonylchloride as residue.

EXAMPLE 14

This example illustrates the preparation of the sulfonamide of polyethylene imine of 32,000 $\overline{Mn}$. A solution of 0.5 mole of polypropyl allylic type sulfonylchloride (hydrocarbon moiety of 800 $\overline{Mn}$) in n-hexane and saturated species of 800 $\overline{Mn}$ polypropene is obtained as in Example 13. To this solution there is added dropwise a solution of 0.5 mole of said polyethylene imine in pyridine so that the exothermic reaction does not exceed 100°F. After addition of the solution of polyethylene imine, the resulting mixture is heated to a temperature of 300°F. and nitrogen gas is injected into the liquid and pyridine is removed with some of the solvent. The residual liquid, a solution of the sulfonamide of the polyethylene imine, is cooled to 100°F., 0.25 mole of calcium hydroxide is added with stirring, and the resulting slurry of calcium chloride and unreacted calcium hydroxide is filter using a diatomite filter aid. Removal of the remainder of the solvent from the filtrate leaves the sulfonamide of the polyethylene imine.

EXAMPLE 15

This example illustrates the preparation of the bis-sulfonamide of ethylene diamine. The method of Example 14 is repeated except that 0.25 mole of ethylene diamine is used in place of 0.5 mole of polyethylene imine. The residue remaining after removal of pyridine, chloride in as calcium chloride and solvent is the bis-sulfonamide of ethylene diamine in which sulfonamide the hydrocarbon moiety from polypropene has 800 $\overline{Mn}$ and the sulfur of the sulfonic acid is attached to a carbon of the hydrocarbon chain to provide the allylic substitution hereinbefore illustrated.

Polypropyl sulfonic acids, sulfonyl chloride and β-chlorosulfonic acids and their sulfonyl chlorides can be readily prepared from polypropenes in the manner hereinbefore disclosed and illustrated.

The utility of the present inventive sulfonamides is illustrated by the following four tests and their results: Spot Dispersancy Test, Panel Coker Test and Inclined Plane Test.

The Spot Dispersancy Test is conducted with the dispersant candidate and used engine crankcase lubricating oil containing sludge typical of used crankcase oil from long (5000–6000 mile) interval between crankcase drains, for example crankcase drain oil drained following completion of a crankcase oil tested in a Ford V8, 289 cubic inch displacement engine having crankcase vented through PCV valve into fuel induction system and run under Sequence conditions. Such Ford 289 Test is a standardized industry accepted crankcase lubricating oil test. The resulting used oil contains substantial amounts of in-service formed sludge. The used oil is stirred to a uniform mixture, aliquot samples are withdrawn, 0.5 gram of the sulfonamide dispersant candidate is added and this mixture is stirred and heated for 4 hours at a temperature of 300°F. An aliquot sample with no added dispersant is treated in the same manner and used as a control. A small amount, 5 drops, of the stirred and heated used oils are each deposited on separately marked areas of blotting paper which is then left undisturbed for 3 hours. This time permits development in each marked area of an inner sludge ring and an outer oil ring. The diameters of these rings ($Ds$ for sludge ring and $Do$ for oil ring) are measured and the values of the ratios $Ds/Do \times 100$ (to obtain whole numbers are calculated). The dispersancy efficiency of the candidate to disperse sludge can be qualitatively evaluated by comparison of the $Ds/Do \times 100$ (ring ratio) values to the control and to like sludgy oils treated in the same manner but containing recognized efficient oil-soluble dispersant addition agent as a second basis for comparison. Such use of recognized efficient dispersant is hereafter called Comparative Example.

Several species of the present inventive sulfonamide products are tested in the Spot Dispersancy Test, as is a Control Sample and a Comparative Sample wherein the recognized dispersant is 0.5 gram high molecular weight Mannich Base from condensation reaction of formaldehyde, polyalkylene polyamine and polybutyl-substituted (polybutyl substituent of 1836 $\overline{Mn}$) phenol. The results of these tests are shown in TABLE I.

TABLE I

| SPOT DISPERSANCY TEST | |
|---|---|
| Example | Ring Ratio Value[1] |
| Control | 55–65 |
| Comparative | 80–90 |
| 5 | 86–96 |
| 2 | 76–91 |
| 10 | 90–100 |
| 8 | 90–100 |

[1]Such Ring Ratio Values are the range of those values from duplicated tests with same used oil.

The above data for products of Examples 2, 5, 8 and 10 indicate that the present inventive high molecular weight polymeralkane sulfonamides have excellent dispersancy for sludge formed in engine and crankcase during long service use of crankcase lubricating oil.

The Panel Coker and Inclined Plane Tests are used to determine high temperature stability of formulated oils containing a candidate additive and the candidate additive. In the Panel Coker Test the formulated lubricating oil at about normal crankcase operating temperature is splashed from an oil sump onto the surface of a polished steel plate heated to a temperature of 600°F. From the nature and amount of solids deposited on the plate the qualitative oxidative stability of the formulated oil and additive candidate are evaluated. The surface of the plate receiving oil splashed from the sump through air is evaluated on a scale of 0–10 wherein the value of 0 means heavy coke-like solids deposit and 10 means a clean surface. The duration of the oil splashing is 2 hours.

The Inclined Plane Test is conducted by permitting formulated oil containing the additive candidate to flow down as a thin film in a aluminum trough having a flat surface of about 0.5 inch wide and vertical side walls each of about 0.5 inch. The trough is heated to a temperature of 500°F., inclined at an angle of about 45° and the formulated oil is permitted to flow from the top of the trough to its bottom where the oil run off is collected. The amount of oil used is 10 ccs. and the duration of oil flow is about one hour. At the end of this test the trough is examined for varnish deposit on the flat bottom and for indications of oil creep over the vertical walls of the trough. Oil creep is evaluated on a letter scale of A through D with A measuring no creep over and only a slight creep up the walls and D meaning substantial oil creep over the walls. Deposit on the flat bottom surface of the trough and its extent down said surface is evaluated on a value scale of 0–10 with a value of 0 being a heavy dark deposit for substantially the length of the trough and the value of 10 being a clean bottom surface.

The formulated oil used in the Panel Coker Test and the Inclined Plane Test is a MS III formulation containing additives other than the candidate additive being tested of known high temperature and oxidative stability at the temperatures of the tests. The formulated oil used in these tests contains 4% of the sulfonamide candidate additive. The results of these tests are shown in TABLE II.

TABLE II

MS III Oil in COKE PANEL AND INCLINED PLANE TESTS

| Candidate Tested | Panel Coker Value | Inclined Plane Value |
|---|---|---|
| Example 2 | 6 | 7.0A |
| Example 5 | 8 | 8.5A |
| Example 8 | 8 | 8.6A |
| Example 10 | 6.5 | 9.8A |
| Comparative[1] | 5.5A | 9.8B |

This Comparative additive was the high molecular weight Mannich product previously described and its concentration was 4%.

A thermal and oxidation stability test closely correlatable to actual in-service engine usage is the "Hot Tube Test". In this test the formulated oil containing the candidate addition agent and other non-detergent addition agents of known oxidation and thermal stabilities commonly used in crankcase lubricant oils is caused to flow downwardly as a film on the internal wall of a vertical glass tube 20 inches long and 8 mm diameter at a rate of 0.1 cc per minute. Of that 20 inch length 6 inches are surrounded by a furnace to a temperature of 495°F. The duration of the test is 100 minutes and air at 20 cc per minute is also passed downwardly through the tube. After the end of the 100 minute test period, the tube is cooled to ambient temperature, rinsed with hexane to remove hexane soluble deposits, if any, and the appearance of the tube is evaluated as to varnish area and intensity. This evaluation is on a scale where 10A is a perfectly clean tube, the numbers rating refers to varnish area on the heated portion of the tube and the letter value refers to varnish formed on the cooler tube portion below the furnace heated tube length. The lower the numerical values and the high the letter rating (A, B, C, D etc.) the poorer is the oxidation and thermal stability of the candidate additive. The candidate inventive sulfonamides and comparative high molecular Mannich Base condensation product before described are tested at 4% concentration. The results of these tests are shown in Table III.

TABLE III

| Candidate Tested | HOT TUBE TEST Rating Heated Area | Value Cool Tube Area |
|---|---|---|
| Comparative | 7.7– | A |
| Example 2 | 8.5 | B |
| Example 5 | 9.9 | A |
| Example 8 | 8.6 | A |
| Example 10 | 9.8 | A |

The above data indicate that the present inventive sulfonamides have higher oxidative and thermal stabilities than high molecular weight Mannich Base condensation product.

The invention claimed is:

1. An aliphatic hydrocarbon sulfonic acid of the structure:

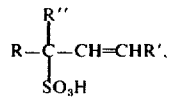

wherein R is an alkyl hydrocarbon group, R' and R'' are alkyl hydrocarbon group of 1 to 5 carbon atoms and the sum of the weights of R, R' and R'' is a 300–3000 $\overline{Mn}$.

2. The sulfonic acid of claim 1 wherein R is polypropyl or polybutyl and R' and R'' have 1 carbon atom when R is polypropyl or 2 carbon atoms when R is polybutyl.

3. The method of preparing the aliphatic sulfonic acid of the structure

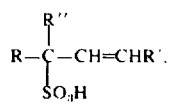

wherein the sum of the weights of R, R' and R'' is 300 to 3000 $\overline{Mn}$, R is an alkyl hydrocarbon group and R' and R'' are alkyl hydrocarbon groups of 1 to 5 carbon atoms, which comprises reacting at a maximum temperature of 90°F. substantially equal molecular proportions of chlorosulfonic acid and a polymeric hydrocarbon of the formula

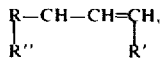

wherein R, R' and R'' are the alkyl hydrocarbon groups of the carbon contents and molecular weight sum as defined in claim 1.

4. The method of claim 3 wherein the polymeric hydrocarbon is a polypropene or polybutene.

* * * * *